United States Patent [19]

Kalbag et al.

[11] Patent Number: 4,656,248

[45] Date of Patent: Apr. 7, 1987

[54] CUPRIC OXIDATION OF 1,6-DIMERCAPTO-CONTAINING PEPTIDES

[75] Inventors: Suresh M. Kalbag, Cupertino; Paul J. Voelker, Sunnyvale, both of Calif.

[73] Assignee: SmithKline Beckman Corporation, Philadelphia, Pa.

[21] Appl. No.: 726,433

[22] Filed: Apr. 23, 1985

[51] Int. Cl.$^4$ ................................................ C07K 7/16
[52] U.S. Cl. ..................................... 530/315; 530/345
[58] Field of Search ................. 260/112.5 R; 530/315, 530/345

[56] References Cited

U.S. PATENT DOCUMENTS

| | | | |
|---|---|---|---|
| 4,367,225 | 1/1983 | Manning et al. | 530/315 |
| 4,469,679 | 9/1984 | Huffman et al. | 530/315 |
| 4,481,194 | 11/1984 | Ali et al. | 530/315 |

OTHER PUBLICATIONS

Cavallini et al., Archives of Biochemistry and Biophysics 130, 354–361 (1969).
A. Hanaki et al., Chem. Pharm. Bull. 19, 1006–10 (1971).
S. L. Feldman et al., J. Inorg. Biochem. 17, 51–60 (1982).
Reid; Organic Chemistry of Bivalent Sulfur, vol. I, pp. 118–119 (1958).

Primary Examiner—Delbert R. Phillips
Attorney, Agent, or Firm—William H. Edgerton; Stuart R. Suter; Alan D. Lourie

[57] ABSTRACT

The preparation of [1-($\beta$-mercapto-$\beta$,$\beta$-cyclopentamethylenepropionic acid)-2-(O-ethyl-D-tyrosine)-4-valine-8-arginine-9-desglycine]vasopressin by oxidation of the corresponding dimercaptan is improved by using a copper II salt.

7 Claims, No Drawings

CUPRIC OXIDATION OF 1,6-DIMERCAPTO-CONTAINING PEPTIDES

This invention is related to an improvement in the chemical preparation of the vasopressin antagonist, [1-(β-mercapto-β,β-cyclopentamethylenepropionic acid)-2-(O-ethyl-D-tyrosine)-4-valine-8-arginine-9-desglycine]vasopressin, and structurally similar vasopressin or oxytocin congeners.

BACKGROUND OF THE INVENTION

U.S. Pat. No. 4,469,679 describes the preparation of the target vasopressin antagonist by oxidation of a linear 1,6-dimercapto-containing peptide using various mild oxidizing agents such as ferricyanide, oxygen or iodine. The use of oxygen involves passage of the gas through the reaction mixture "for several days." Also, extremely dilute reaction conditions are there described as preferred, column 2 lines 47–56. A number of other publications have similar disclosures for preparing vasopressin-like compounds, for example, Manning et al., U.S. Pat. No. 4,367,225 or Ali et al., U.S. Pat. No. 4,481,194.

Another series of publications, such as Cavallini et al., Archives of Biochemistry and Biophysics 130, 354–361, describes the intermolecular oxidation of cysteine to the dimeric cystine by using a copper catalyzed oxidation with the cysteine-$Cu^{II}$ complex being the intermediate catalyst.

As far as we are aware, copper II-catalyzed oxidation has not been applied to form an intramolecular S-S bond previously.

DESCRIPTION OF THE INVENTION

The preparation of vasopressin-oxytocin congeners usually includes an intramolecular oxidation of a linear 1,6-dimercapto-containing peptide to form the cyclic disulfide structure. This is illustrated by the following reaction:

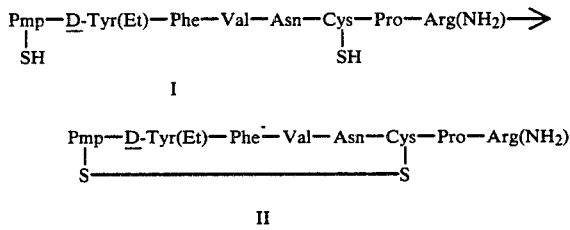

The prior art oxidative methods of forming the vasopressin-oxytocic disulfide ring are satisfactory for laboratory preparations but have some disadvantages for up-scale operations.

For example, the main by-product of the prior art reaction conditions is the dimeric product formed by intermolecular sulfide ring formation. Side oxidation can be minimized by high dilution techniques, as discussed above, however, on a large scale, use of excess solvent is expensive. Use of oxygen or air is very slow. Use of ferricyanide is expensive. The improvement of the present invention is believed to solve such prior art problems.

The linear dimercaptopeptide, such as I, is dissolved in an inert, polar solvent in which both it and the cupric II salt are substantially soluble. Such solvents include water, lower alkanols especially methanol, ethanol or isopropanol, dimethylformamide, dimethylacetamide, acetone or mixtures thereof. Methanol has proved to be an excellent solvent. Only 250 ml of methanol per gram of liner dimercaptan need be used.

The reactants are usually used in a one to one-half or one to one reactant to copper stoichiometric ratio. The cupric salt may be used in excess with little disadvantage in the course of the reaction. Any cupric salt which is commercially available and which is soluble in an acceptable solvent system in which the dimercaptopeptide is also soluble may be used. Examples are copper II chloride, sulfate, bromide, acetate, butyrate, formate, lactate, tartrate, nitrate and the like. The copper II salt must be soluble in the selected solvent system and must dissociate in that system to an extent that the activated Cu II-peptide complex can be formed.

The reaction is carried out conveniently at room temperature. Temperature variation does not beneficially affect the reaction since the cyclic product forms quickly, often in a few minutes when the I→II reaction mixture is analyzed by high performance liquid chromatography (HPLC) (50% 0.03 M ammonium acetate, pH 7 in acetonitrile).

The reaction product is isolated in good yield by standard peptide isolation and purification methods. Copper ion are best removed from the mixture by countercurrent-distribution (CCD) using butanol/acetic acid/water (4:1:5). Various copper II trapping agents have been used to separate inorganic salt from the peptide. Examples of these are neocuproine, potassium iodide, cation chelating resins and thioacetamide.

The improvement reaction of this invention can be applied to any linear dimercaptopeptide which contains a 1,6-dimercapto system. The latter, in turn, forms a 6 unit ring closed with a disulfide link. Such compounds, particularly, are any vasopressin or oxytocin agonist or antagonist in addition to the species of the reaction described herein, I→II.

The linear 1,6-dimercapto-containing peptide (such as I) may be used in deprotected form as well as with protective groups at any reactive center not participating in the oxidative cyclization. Also as in the case of the species, I, any acid addition salt may be used when a basic center is present in the peptide. Best results are used with this species when the acetate salt is used. This salt is usually isolated in the reaction sequence used to prepare the linear starting material, as described in U.S. Pat. No. 4,469,679. The anion of the acid should be one which will not interfere with the cupric oxidation. For example, the hydrogen fluoride salt of I, which is often the product isolated after splitting the linear peptide from a supporting resin, gives less desirable cyclization results.

The mechanism of action of the claimed improvement has not be clarified. We assume that the reactive intermediate is a 1 to 1 cupric-dimercaptan complex. Any cuprous ion by-product of the reaction may be oxidized to copper II by nascent oxygen.

The following examples are illustrative of the operation of this invention and are not intended to be limiting. All temperatures are in degrees Centigrade. Experimental techniques and nomenclature are those common in the peptide art.

EXAMPLE 1

General method: A linear 1,6-dimercapto-containing hexapeptide is dissolved in methanol in a ratio of 200 ml/g of peptide and is treated with 1 equivalent of cupric sulfate pentahydrate in methanol. The total volume of the reaction mixture is about 250 ml of methanol per gram of linear peptide. The ensuring oxidation is complete in as little as 1 minute with no evidence of reduced peptide or observable dimer formation. The solution is filtered through a filter aid and the filtrate evaporated in vacuo. After drying, the residue is taken up in water and again filtered. The aqueous filtrate is freeze-dried and lyophilized to give the cyclized vaopressin or oxytocin congener in 40–50% crude yield. The product is further purified by counter current distribution or gel filtration.

EXAMPLE 2

To a slightly turbid solution of 5.72 g (56% pure) HOAc-Pmp-D-Tyr(Et)-Phe-Val-Asn-Cys-Pro-Arg(NH$_2$) in 1144 ml of methanol was added one stoichiometric equivalent of cupric sulfate pentahydrate in 286 ml of methanol. The ensuing black cloudy mixture was allowed to stir at room temperature for 5 minutes, then concentrated and dried under vacuum overnight. The black solid was washed with 10% acetic acid until the filtrate was clear. The solid was then washed with glacial acetic acid until a small amount of shiny black residue remained. Both acetic acid washes were lyophilized separately. The 10% wash afforded 540 mg (15% pure) and the glacial wash afforded 5.02 g (23% pure) of the cyclic disulfide. Based on purity of the starting material, there was afforded a 38% yield of

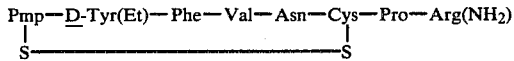

The 5.01 g fraction was loaded onto a P-2 polyacrylamide gel filtration column and eluted with 1 N acetic acid. Three fractions were collected, 3.94 g (10% pure), 750 mg (76% pure), and 150 mg (78% pure). Recovered crude yield was 97%. A sample comparable to that of the 5.01 g fraction was purified using counter-current distribution using butanol/acetic acid/water (4:1:5) to give a purified sample of the cyclic disulfide with copper reduced to 0.0032% by weight.

What is claimed is:

1. In the process of preparing a compound of the formula:

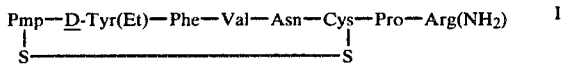

by oxidation of a compound of the formula:

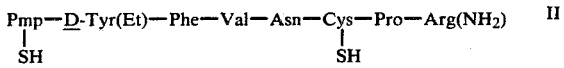

or an acid addition salt thereof, the improvement comprising carrying out said oxidation in the presence of a copper II salt in a solvent system in which compound (II) and the copper II salt are substantially soluble and which is not chemically reactive with either compound II or the copper II salt.

2. The improvement of claim 1 in which the copper II salt is cupric sulfate.

3. The improvement of claim 1 in which the solvent is methanol.

4. The improvement of claim 2 in which the solvent is methanol.

5. The improvement of claim 1 in which compound (II) is in the form of the acetate salt.

6. The improvement of claim 1 in which any copper salt admixed with the product of the process is removed using counter-current distribution.

7. In the process of preparing a vasopressin antagonist compound of the formula:

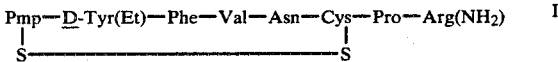

by oxidation of a compound of the formula:

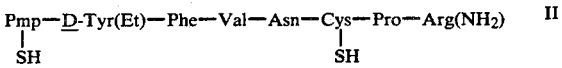

or an acid addition salt thereof, the improvement comprising carrying out the oxidation in the presence of cupric sulfate in methanol in which the compound and cupric sulfate are substantially soluble and which is not chemically reactive with either the compound or the cupric sulfate.

* * * * *